United States Patent [19]

O'Neill et al.

[11] Patent Number: 5,268,181

[45] Date of Patent: Dec. 7, 1993

[54] METHOD OF USING NIACIN TO CONTROL NOCTURNAL CHOLESTEROL SYNTHESIS

[75] Inventors: Victoria A. O'Neill; Kenneth L. Evenstad, both of Wayzata, Minn.

[73] Assignee: Upsher-Smith Laboratories, Inc., Minneapolis, Minn.

[21] Appl. No.: 905,785

[22] Filed: Jun. 29, 1992

Related U.S. Application Data

[60] Continuation-in-part of Ser. No. 536,184, Jun. 11, 1990, Pat. No. 5,126,145, which is a division of Ser. No. 337,460, Apr. 13, 1989, abandoned.

[51] Int. Cl.$^5$ .................... A61K 9/22; A61K 9/30; A61K 31/455; A61K 47/38
[52] U.S. Cl. .................................. 424/465; 424/468; 424/469; 424/470; 424/488; 424/474; 424/475; 424/486; 424/499; 424/502; 514/356; 514/824
[58] Field of Search ............... 424/464, 465, 474, 476, 424/489; 514/356, 824

[56] References Cited

U.S. PATENT DOCUMENTS

| | | | |
|---|---|---|---|
| 3,870,790 | 3/1975 | Lowey et al. | 424/19 |
| 4,166,902 | 9/1979 | Ferruti et al. | 536/48 |
| 4,259,314 | 3/1981 | Lowey | 424/19 |
| 4,369,172 | 1/1983 | Schor et al. | 424/19 |
| 4,389,393 | 6/1983 | Schor et al. | 424/19 |
| 4,432,966 | 2/1984 | Zeitova et al. | 424/477 |
| 4,457,907 | 7/1984 | Porter | 424/477 |
| 4,568,547 | 2/1986 | Herschler | 424/465 |
| 4,680,323 | 7/1987 | Lowey | 524/43 |
| 4,704,285 | 11/1987 | Alderman et al. | 424/468 |
| 4,708,834 | 2/1987 | Cohen et al. | 514/356 |
| 4,749,575 | 6/1988 | Rottman | 424/453 |
| 4,752,479 | 6/1988 | Briggs | 424/441 |
| 4,756,911 | 7/1988 | Drost et al. | 424/472 |
| 4,795,642 | 1/1989 | Cohen et al. | 424/468 |
| 4,911,917 | 3/1990 | Kuhrts | 424/455 |
| 4,920,115 | 4/1990 | Nestler et al. | 424/10 |
| 4,920,123 | 4/1990 | Beyer, Jr. | 514/178 |
| 4,950,689 | 8/1990 | Yang et al. | 514/255 |
| 4,965,252 | 10/1990 | Kuhrts | 424/439 |
| 5,010,105 | 4/1991 | Lee | 514/54 |
| 5,011,947 | 4/1991 | Catt et al. | 514/510 |
| 5,023,245 | 6/1991 | Kuhrts | 424/439 |
| 5,030,653 | 7/1991 | Trivedi | 424/439 |
| 5,034,528 | 7/1991 | Izydore et al. | 514/510 |
| 5,049,696 | 9/1991 | Lee et al. | 544/223 |
| 5,096,714 | 3/1991 | Kuhrts | 560/75 |
| 5,110,817 | 5/1992 | Beyer et al. | 424/439 |
| 5,110,940 | 6/1992 | Sit et al. | 514/255 |
| 5,116,610 | 5/1992 | Broaddus | 548/25212 |
| 5,126,145 | 6/1992 | Evanstad et al. | 424/78.12 |

FOREIGN PATENT DOCUMENTS 0109320 6/1986 European Pat. Off. .

OTHER PUBLICATIONS

*Methocel as a Binding Agent for Table Production by Wet Granulation*, a publication of The Dow Chemical Company, 1985.

*Formulating for Controlled Release with Methocel Cellulose Ethers*, a publication of The Dow Chemical Company, 1987.

J. D. Alderman et al., "Effect of a Modified, Well-Tolerated Niacin Regimen on Serum Total Cholesterol, Higher Density Lipoprotein Cholesterol and the Cholesterol to High Density Lipoprotein Ratio", *Am. J. Cardiology*, 64:725 (1989).

*Ann. of Intern. Med.*, "National Education Programs Working Group Report on the Management of Patients with Hypertension and High Blood Cholesterol", 114:224 (1991).

*Arch. Intern. Med.*, "Report of the National Cholesterol Education Program Expert Panel on Detection, Evaluation, and Treatment of High Blood Cholesterol in Adults", 148:36 (1988).

(List continued on next page.)

Primary Examiner—Thurman K. Page
Assistant Examiner—James M. Spear
Attorney, Agent, or Firm—Merchant, Gould, Smith, Edell, Welter & Schmidt

[57] ABSTRACT

The invention provides a therapeutic method to treat hyperlipidemia by administering to a human patient a single daily dose of a prolonged release dosage form of niacin, so that nocturnal cholesterol synthesis is effectively suppressed.

11 Claims, No Drawings

OTHER PUBLICATIONS

I. Bjorkhem et al., "Correlation Between Serum Levels of Some Cholesterol Precursors and Activity of HMG-CoA Reductase in Human Liver", *J. Lipid Research,* 28:1137 (1987).

D. B. Hunninghake, editor, *Issues in Cholesterol Management: Reappraisal of Niacin,* Upsher-Smith Laboratories, Inc. (publisher) (1990).

T. A. Miettinen, "Election of Changes in Human Cholesterol Metabolism", *Ann. Clin. Res.,* 2:300 (1970).

T. A. Miettinen, "Diurnal Variation of Cholesterol Precursors Squalene and Methyl Sterols in Human Plasma Lipoproteins", *J. Lipid Res.,* 23:466 (1982).

T. A. Miettinen, "Cholesterol Precursors and Their Diurnal Rhythm in Lipoproteins of Patients with Jejuno-Ileal Bypass and Ileal Disfunction", *Metabolism,* 34:425 (1985).

M. J. Robinson, "Coating of Pharmaceutical Dosage Forms", *Remington's Pharmaceutical Sciences,* A. Osol, ed., Mack Publishing Co., Easton, Pa., (16th edition) (1980) at pp. 1585-1593.

J. C. Rosa, *Circulation,* "The Cholesteral Facts", 81:1721 (1990).

S. Yusek et al., "Overview of Results of Randomized Clinical Trials in Heart Disease", *JAMA,* 260:2259 (1988).

H. G. Zimmerman et al., "Drugs Used in Cardiovascular Disease", *Hepatotoxicity,* Appleton-Century-Crofts, New York, N.Y. (1978) at pp. 510-512.

METHOD OF USING NIACIN TO CONTROL NOCTURNAL CHOLESTEROL SYNTHESIS

CROSS-REFERENCE TO RELATED APPLICATION

This application is a continuation-in-part of U.S. patent application Ser. No. 7/536,184, filed Jun. 11, 1990, now U.S. Pat. No. 5,126,145, which is a divisional application of Ser. No. 7/337,460, filed Apr. 13, 1989, abandoned.

BACKGROUND OF THE INVENTION

Guidelines developed by the National Cholesterol Education Program's Expert Panel on Detection, Evaluation, and Treatment of High Blood Cholesterol in Adults, as reported in *Arch. Intern. Med.*, 148, 36 (1988), identified elevated cholesterol and low-density lipoprotein cholesterol (LDL-C) concentrations as the major targets for cholesterol-lowering therapy. The importance of cholesterol reduction in patients with overtly manifest coronary artery disease cannot be overstated, since virtually every major epidemiological study performed to date has shown a significant correlation between the level of serum cholesterol at the time of entry and the risk of subsequent coronary disease. For example, see J. C. Rosa, *Circulation*, 81, 1721 (1990).

The results of 22 randomized cholesterol-lowering clinical trials to reduce the risk of coronary heart disease indicate an average reduction of 23 percent in the risk of non-fatal myocardial infarction and cardiac death in treated compared with control patients. In particular, a 10 percent decrease in the cholesterol level was associated with a reduction of approximately 20 percent in the incidence of new coronary events (S. Yusef et al., *JAMA*, 260, 2259 (1988)).

Present therapeutic guidelines include the recommendation that cholesterol-lowering drugs should be considered when cholesterol and low density lipoprotein-cholesterol (LDL-C) levels remain significantly elevated after six months of appropriate dietary therapy. For example, see "National Education Programs Working Group Report on the Management of Patients With Hypertension and High Blood Cholesterol," *Ann. of Intern. Med.*, 114, 224 (1991).

Niacin is commonly employed to treat hypercholesterolemia because it lowers total serum cholesterol, low density lipoproteins (LDL) and triglycerides, and the attendant risk of cardiovascular disease. In addition, recent observations have shown that niacin is effective to increase low levels of high density lipoproteins (HDL).

Niacin is nicotinic acid (pyridine-3-carboxylic acid). It inhibits lipoprotein synthesis by preventing the secretion of very low density lipoprotein (VLDL) from the liver. Because VLDL is a precursor for the intermediate density lipoproteins (IDL) and LDL, the circulating levels of all of the atherogenic lipoprotein fractions are decreased. In addition, niacin decreases levels of lipoprotein a, which has been associated with a two-fold increase in the relative risk of coronary artery disease. The rate-limiting enzyme in cholesterol biosynthesis is hepatic hydroxymethylglutaryl coenzyme A reductase (HMG-CoA reductase). For example, I. Bjorkhem et al., in *J. Lipid Res.*, 28, 1137 (1987) reported high correlations between the relative concentrations of cholesterol precursors such as free lanosterol and lathostenol, cholesterol synthesis and the activity of HMG-CoA reductase.

A wide variety of niacin preparations are available from different manufacturers, each having unique bioavailability, pharmokinetic, and safety profiles. In general, lower doses of niacin (1-3 g/day) are used, because they maintain beneficial lipid effects while minimizing adverse side affects. For example, niacin causes prostaglandin-mediated vasodilation, leading to flushing, warm skin, itching rash and tingling. Aspirin is effective in some cases to control these effects, as is gradual dosage escalation. High niacin (4.3 g/day) also causes substantial incidences of gastrointestinal effects, such as constipation, nausea and heartburn.

Although the vasodilatory and gastrointestinal effects of niacin can either be modulated or are absent at dosage levels which are still effective to lower cholesterol, abnormalities in liver function tests have been observed in 19% of patients treated with daily doses of 2.0 g or less of niacin. (J. D. Alderman et al., *Am. J. Cardiol.*, 64, 725 (1989)). For example, serum transaminase can increase to levels at which niacin must be discontinued. Niacin has also produced hepatocellular degeneration and necrosis. The precise mechanism of injury is not known. However, a dose-relationship suggests some intrinsic hepatotoxic potential that is modified by individual patient susceptibility. See, H. J. Zimmerman, in *Hepatotoxicity*, Appleton-Century-Crofts; New York, N.Y. (1978) at pages 510-512.

Therefore, a need exists for a method to administer niacin in doses effective to lower serum lipids, while minimizing or eliminating such dose-limiting side effects.

BRIEF DESCRIPTION OF THE INVENTION

The present invention provides an improved therapeutic method to lower serum lipids or lipid components selected from the group consisting of cholesterol, lipoprotein a, total triglycerides and/or low-density lipoprotein-cholesterol (LDL-C) comprising administering to a human in need of such treatment an effective amount of niacin, in a controlled release dosage form. Preferably, the amount of niacin administered is also effective to raise the levels of high density lipoprotein-cholesterol (HDL-C). The niacin is administered in a single dose during a time period during the day when the niacin levels subsequently achieved in vivo are effective to substantially lower the levels of said serum lipids or lipid components which are primarily nocturnally biosynthesized, e.g., between about 8 p.m.-10 p.m. and 6 a.m.-8 a.m. Preferably, the niacin is administered at, or immediately following, the evening meals and before bedtime, i.e., between about 4 p.m. and 8 p.m.

The amount of niacin that is administered is effective to substantially lower at least one serum lipid or lipid component, while not inducing hepatotoxicity at levels which would require the therapy to be discontinued. For example, in accord with the present method, a lowering of cholesterol and LDL-cholesterol of 10-20% each, and an elevation of HDL-C of about 10-20% is believed to be achievable in hypercholesterolemic patients (>250 mg/dl serum) at single total daily doses of niacin (750 mg-2.0 g) that are 25-75% lower than the total spaced daily dose of niacin that would be required to achieve the same efficacy. In other words, a single 750 mg-1.5 g dose of niacin administered between about 4 p.m.-8 p.m. is expected to be as effective as an equal or higher daily dosage of niacin daily, administered in two to four divided doses between, i.e., 8 a.m. and 8 p.m.

Furthermore, because at least a majority of the niacin is released and metabolized in vivo during a limited preselected period of about 10–12 hours, the liver is not exposed to the constant levels of niacin which result during administration of long-term, spaced daily doses of niacin. Thus, the likelihood that the patient will develop dose-limiting hepatotoxicity is greatly decreased.

The present invention also provides a kit comprising packaging material and a plurality of said controlled-release unit dosage forms of niacin contained within said packaging material, and wherein said packaging material also comprises instruction means, therein or attached thereto, instructing that one or more, e.g., about 1–4, of said unit dosage forms be ingested by a human patient once daily, with the evening meal, or after the evening meal and before bedtime, in order to lower serum lipids or lipid components selected from the group consisting of cholesterol, lipoprotein a, total triglycerides and/or low-density lipoprotein-cholesterol, or to raise high-density lipoprotein cholesterol. Said instruction means can be a printed label or package insert, a cassette tape, a video tape or a magnetic disk.

All percentages are weight percentages of the total tablet weight unless otherwise noted.

DETAILED DESCRIPTION OF THE INVENTION

The ability of the present single daily dose method to lower cholesterol levels achievable heretofore only with higher single or divided doses is believed to be due at least in part to the observation that, in experimental animals, the rate of cholesterol and cholesterol precursor biosynthesis is highest after midnight and lowest during the morning and early afternoon. In the case of humans, T. A. Miettinen, in *J. Lipid Research*, 23, 466 (1982) found that during the night and early morning, the levels of a number of biosynthetic precursors of cholesterol were several times higher than during the daytime. Thus, the peak plasma squalene and methyl sterol levels occurred at midnight and 4 a.m. Since the equivalent circadian rhythm variation in mammals is caused by diurnal changes in the activity of the cholesterol biosynthesis rate-limiting enzyme hydroxymethyl-glutaryl coenzyme A reductase (HMG-CoAR), Mietinen concluded that the variation in precursors which was observed is most likely due to changes in cholesterol synthesis, and that circadian rhythm also regulates human cholesterol production. The accompanying cyclic accumulation of the precursors in the hepatic and intestinal epithelial cells leads to their increased availability for incorporation into blood lipoproteins. Thus, the efficacy of the present invention is grounded on our belief that triglyceride and cholesterol synthesis are predominantly nocturnal events. Thus, while the present method provides little or no niacin in vivo during the daytime, the rate of normal human cholesterol synthesis is believed to be as much as 3–7 times lower during this period.

In order to effectively suppress cholesterol synthesis during a period when the patient would not be readily able or willing to periodically ingest oral niacin, the niacin is preferably administered following the evening meal and prior to bedtime in a single dose. The single dose of niacin preferably is administered via ingestion of one or more controlled release unit dosage forms, so that effective niacin levels are maintained throughout the night, i.e., during the peak periods of serum lipid/lipid component biosynthesis.

A useful controlled release tablet is disclosed in commonly assigned Evenstad et al. (U.S. Pat. No. 5,126,145), which is incorporated by reference herein. This tablet comprises, in admixture, about 5–30% high viscosity hydroxypropyl methyl cellulose, about 2–15% of a water-soluble pharmaceutical binder, about 2–20% of a hydrophobic component such as a waxy material, e.g., a fatty acid, and about 30–90% niacin.

More specifically, one such useful controlled release tablet comprises: (a) about 5–20 percent by weight hydroxypropyl methylcellulose having a viscosity of about 10,000 CPS or greater, a substitution rate for the methoxyl group of about 7–30% and a substitution rate for the hydroxypropoxyl group of about 7–20%; (b) about 2–8 percent hydroxypropyl methylcellulose having a viscosity of less than about 100, CPS methyl cellulose, or polyvinyl pyrollidone; (c) about 5–15 percent by weight hydrogenated vegetable oil or stearic acid; and (d) about 30–90% niacin.

High viscosity water-soluble 2-hydroxypropyl methyl cellulose (HPMC) is particularly preferred for use in the present tablets and in the controlled-release tablet coating, due to its sustaining properties with respect to niacin release. A particularly preferred high viscosity HMPC has a nominal viscosity, two percent solution, of about 100,000 CPS, methoxyl content of about 19–24, a hydroxypropyl content of about 7–12 percent, and a particle size where at least 90% passes through a USS 100 mesh screen. (Methocel® K100MCR). Low viscosity HPMC is preferred as the binder component of the tablet. A particularly preferred low viscosity HPMC has a methoxyl content of about 20–30%, a hydroxylpropyl content of about 7–12 percent, and a particle size where 100% will pass through a USS No. 30 mesh screen and 99% will pass through a USS 40 mesh screen (Methocel® EIS). In some cases, a portion of the high viscosity HPMC can be replaced by a medium viscosity HPMC, i.e., of about 2000–8,000 cps.

The viscosities reported herein are measured in centipoises (cps or cP), as measured in a 2% by weight aqueous solution of the cellulose either at 20° C. using a rotational viscometer. A "high viscosity" cellulose ether possesses a viscosity of at least about 10,000 cps i.e., about 50,000–100,000 cps. A low-viscosity cellulose ether possesses a viscosity of less than about 100 cps, i.e., about 10–100 cps.

"Water soluble" for purposes of this application means that two grams of powdered cellulose ether can be dispersed by stirring into 100 grams of water at a temperature between 0° C.–100° C. to provide a substantially clear, stable aqueous composition or dispersion (when the dispersion is brought to 20° C.).

Useful hydrophobic components include natural and synthetic waxes such as beeswax, carnauba wax, paraffin, spermaceti, as well as synthetic waxes, hydrogenated vegetable oils, fatty acids, fatty alcohols and the like.

The controlled release niacin tablets preferably can be formulated to contain 250 mg, 500 mg or 750 mg of niacin, and are ingested orally in a number sufficient to provide a total dosage of about 0.750–2.75 g niacin, preferably, about 1.5–2.0 g of niacin.

Preferably, these tablets will release about 10–35 wt-% of the total niacin within about 2 hours in an in vitro dissolution test, and about 40-70 wt-% of the total niacin in eight hours.

These controlled released tablets can also be coated so as to further prolong the release of the niacin into the gastrointestinal tract, or to prevent its release into the stomach, in order to prevent or attenuate the gastrointestinal side effects which can accompany niacin administration.

For example, coatings comprising a major portion of a polymeric material having a high degree of swelling on contact with water or other aqueous liquids can be used to further prolong the release of the niacin from the tablets core. Such polymers include, inter alia, cross-linked sodium carboxymethylcellulose (Acdisol-FMC), cross-linked hydroxypropylcellulose, hydroxymethylpropylcellulose, e.g., Methocel ® K15M, Dow Chem. Co., carboxymethylamide, potassium methylacrylate divinylbenzene copolymer, polymethyl methacrylate, cross-linked polyvinylpyrrolidine, high molecular weight polyvinylalcohol, and the like. Hydroxypropylmethyl cellulose is available in a variety of molecular weights/viscosity grades from Dow Chemical Co. under the Methocel ® designation. See also, Alderman (U.S. Pat. No. 4,704,285). These polymers may be dissolved in suitable volatile solvents, along with dyes, lubricants, flavorings and the like, and coated onto the prolonged release tablets, e.g., in amounts equal to 0.1-5% of the total tablet weight, by methods well known to the art. For example, see *Remington's Pharmaceutical Sciences,* A. Osol, ed., Mack Publishing Co., Easton, Pa. (16th ed. 1980) at pages 1585-1593.

Enteric coatings can also be provided to the prolonged release tablets to prevent release of the niacin until the tablet reaches the intestinal tract. Such coatings comprise mixtures of fats and fatty acids, shellac and shellac derivatives and the cellulose acid phthlates, e.g., those having a free carboxyl consent of 9-15%. See, *Remington's* at page 1590, and Zeitova et al. (U.S. Pat. No. 4,432,966), for descriptions of suitable enteric coating compositions.

The invention will be further understood by reference to the following Examples which include preferred embodiments.

EXAMPLE I 750 mg. niacin tablets were formed having the following components:

| Ingredient | % by Weight | Mg./Tablet |
|---|---|---|
| Niacin (Lonza) | 73.07 | 750.0 |
| Hydroxypropyl Methylcellulose 2910 Methocel ® E15LV, Dow) | 2.50 | 25.7 |
| Hydroxypropyl Methylcellulose 2208 Methocel ® K100MCR, Dow) | 9.74 | 100.0 |
| Hydrogenated Vegetable Oil (Lubritab ®, Mendell) | 11.56 | 118.7 |
| Glyceryl Behenate (Compritol ® 888) | 0.50 | 5.1 |
| Magnesium Stearate (Mallinckrodt) | 1.50 | 15.4 |
| FD&C Red #40 Lake Dye (40%) (Colorcon ®) | 0.13 | 1.3 |
| Colloidal Silicon Dioxide (Syloid ® 244) | 1.00 | 10.3 |

To form the tablets, 16 liters of water was heated to 95° C. in a stainless steel container. The Methocel ® E15LV powder was slowly added while mixing until homogenous suspension was obtained. The impeller speed was adjusted to avoid excessive air from entering the solution through the vortex.

Very cold water, 48 liters of it, was slowly added and the mixture was mixed thoroughly until a clear solution was obtained and the temperature was below 20° C. Mixing continued for an additional 20 minutes.

The hydrogenated vegetable oil was sized through a USS No. 16 screen and added to a mixer. The dye was added to the mixer and mixed until the color distribution was uniform, about 5 minutes. The color mix was then transferred to a ribbon blender. The niacin powder was added to the ribbon blender and mixed for about 10 minutes. The Methocel ® K1100MCR was then added and mixed for an additional 10 minutes.

The Methocel ® E15LV solution was sprayed in and then mixed for 1 minute. The resulting wet granulation was then sized through a USS No. 16 screen.

The sized wet granulation was spread lightly on trays, at approximately 2 kilograms per tray. The granulation was dried in an oven at 230° F. to a moisture content of less than 5 percent. The oven-dried granulation was then sized through a USS No. 12 screen. After sizing, the granulation was collected in double poly-lined drums.

Three approximately 200 kilogram batches were formed in the above manner, each utilizing 149.06 kilograms niacin, 3.97 kilograms Methocel ® E15LV, 19.87 kilograms Methocel ® K100MCR, 24.84 kilograms Lubritab ® hydrogenated vegetable oil, and 0.26 kilograms FD&C Red Dye #40 Lake 40% pure dye. These batches were weighed, and combined in a ribbon blender. The plasticizer glyceryl behenate (3.0 kilograms) and 3.0 kilograms magnesium stearate were then added to the ribbon blender and the mixture was mixed for 5 minutes. The resulting product was tableted using a standard rotary press into tablets of 750 mgs niacin.

EXAMPLE II

Niacin tablets (750 mg) were formed as follows:

| Ingredient | Mg/Tablet | Kilograms |
|---|---|---|
| Niacin (Lonza) | 750.00 | 312.5 |
| Hydroxypropyl Methycellulose 2910 Methocel ® E15LV, Dow) | 24.00 | 10.0 |
| Hydroxypropyl Methylcellulose 2208 Methocel ® K100MCR, Dow) | 94.10 | 39.2 |
| Hydrogenated Vegetable Oil (Lubritab ®, Mendell) | 62.40 | 26.0 |
| FD&C Red #40 Lake Dye (40%) (Colorcon) | 0.70 | 0.3 |

The niacin tablets of Example II were formulated by the fluid bed process. Half of the above quantities were used for the first granulation. In this granulation, 33.000 kilograms deionized water were added to a stainless steel steam kettle and heated to 95° C. While mixing (but avoiding excess foaming), the Methocel ® E15LV and dye were added to the water. Cold deionized water (67.0 kilograms) were then added and mixing continued for about 20 minutes. The mixture was cooled to 21° C.

To the fluid bed container were added the niacin, Methocel ® K100MCR, and Lubritab ® hydrogenated vegetable oil. These three components were granulated with the Methocel ® E15LV solution. After exhausting the granulating solution, the material in the fluid bed containers was dried to less than 1% moisture.

The dried material was transferred to clean polylined containers. Using the Sweco Sifter, fitted with a 12 mesh screen, the granulation was sized into clean plastic-lined drums.

A second batch of granulation was formed in an identical manner using the remaining half of the components. The two granulations were then added to a ribbon blender. These components were blended for 5 minutes. Magnesium stearate (6.0 kilograms), 2.0 kilograms glycerol behenate, and 4.0 kilograms colloidal silicon dioxide filler were added to the ribbon blender and mixed for 5 minutes. The material was transferred to clean plastic-lined drums and later tabletted into tablets containing 750 milligrams niacin.

Two other formulations are shown below.

EXAMPLE III

| Ingredient | Milligrams/Tab | Percent |
| --- | --- | --- |
| Niacin | 750.0 | 78.125 |
| Methocel ® E15LV (hydroxypropyl methylcellulose) | 24.0 | 2.50 |
| Methocel ® K1000MCR (hydroxypropyl methylcellulose) | 94.1 | 9.80 |
| Lubritab ® (hydrogenated vegetable oil) | 62.4 | 6.50 |
| FD&C Red #40 dye | 0.7 | 0.075 |
| Magnesium Stearate | 14.4 | 1.50 |
| Compritol ® (glyceryl behenate) | 4.8 | 0.50 |
| Syloid ® 244 (colloidal silicon dioxide) | 9.6 | 1.00 |

Tablets having the formulation of Example III were made using conventional and fluid bed granulating techniques in a production mode.

The tablets were dissolved using a Hanson Dissolution Apparatus with a U.S.P. rotating basket at 100 rpm in 900 ml water at 37° C. Samples were taken from each dissolution vessel at 1, 2, 4, 8, 12 and 24 hours, and analyzed by UV for nicotinic acid content. The results show a desirable release pattern.

EXAMPLE IV

| Ingredient | Milligrams/Tab | Percent |
| --- | --- | --- |
| Niacin | 750.0 | 76.220 |
| Methocel ® E15LV (hydroxypropyl methylcellulose) | 24.0 | 2.439 |
| Methocel ® K100MCR (hydroxypropyl methylcellulose) | 94.1 | 9.561 |
| Lubritab ® (hydrogenated vegetable oil) | 86.4 | 8.780 |
| FD&C Red #40 dye | 0.7 | 0.073 |
| Magnesium Stearate | 14.4 | 1.463 |
| Compritol ® (glyceryl behenate) | 4.8 | 0.488 |
| Syloid ® 244 (colloidal silicon dioxide) | 9.6 | 0.976 |

Tablets having the formulation of Example IV were made using conventional granulating techniques in the laboratory.

EXAMPLE V

| Ingredient | By Weight % | Mg/Tablet |
| --- | --- | --- |
| Niacin | 73.07 | 500.00 |
| Methocel ® E15LV (hydroxypropyl methylcellulose) | 2.50 | 17.11 |
| Methocel ® K100MCR (hydroxypropyl methylcellulose) | 9.74 | 66.65 |
| Lubritab ® (hydrogenated vegetable oil) | 11.56 | 79.10 |
| Compritol ® 888 (glyceryl behenate) | 0.50 | 3.42 |
| Magnesium Stearate | 1.50 | 10.26 |
| FD&C Red #40 dye | 0.13 | .89 |
| Syloid ® 244 (colloidal silicon dioxide) | 1.00 | 6.84 |

Tablets having the composition shown in Example V were made using conventional and fluid bed techniques.

EXAMPLE VI

| Ingredient | By Weight % Total | Mg/Tablet |
| --- | --- | --- |
| Niacin | 73.07 | 250.00 |
| Methocel ® E15LV (hydroxypropyl methylcellulose) | 2.50 | 8.55 |
| Methocel ® K100MCR (hydroxypropyl methylcellulose) | 9.74 | 33.32 |
| Lubritab ® (hydrogenated vegetable oil) | 11.56 | 39.55 |
| Compritol ® 888 (glyceryl behenate) | 0.50 | 1.71 |
| Magnesium Stearate | 1.50 | 5.13 |
| FD&C Red #40 dye | 0.13 | .45 |
| Syloid ® 244 (colloidal silicon dioxide) | 1.00 | 3.42 |

Tablets having the composition shown in Example V were made using conventional and fluid bed techniques.

Tablets having the composition shown in Example VI were made using conventional and fluid bed techniques.

EXAMPLE VIII

Projected Clinical Trial

The primary objective of this study will be to compare the efficacy of a single dose slow-release niacin preparation in the reduction of LDL cholesterol with the efficacy of the same total dose given twice daily (b.i.d.). A placebo group will also be included. Clinical efficacy will be considered to be a 15% or greater decrease in LDL from baseline values. Distribution of patients with fractional reductions will also be evaluated. Secondary efficacy parameters will be changes in triglycerides, HDL cholesterol and apolipoprotein levels, and adverse reactions, particularly hepatotoxicity.

For initial inclusion, a patient must exhibit hypercholesterolemia (total cholesterol ≧240 mg/dL) at screening, have normal liver function test results (bilirubin, SGOT and alkaline phosphatase each no more than 1.5 times normal). Only males and non-pregnant, non-lactating females, 18 to 75 years of age will be included, and sexually active females must be either at least one year postmenopausal, sterile, have had an intrauterine device (IUD) in place for greater than two months or be using an approval oral contraceptive. In order to quality for the treatment phase, patients must have a mean LDL cholesterol level of ≧160 mg/dL for the last two baseline visits.

This is a double-blind, placebo controlled, randomized, parallel study. For each subject group, it involves an eight-week baseline period, a one-week "low-dose" period, a dose titration period of four weeks and four weeks of treatment at the highest tolerated dose of niacin (efficacy phase). Following four weeks of treatment at the highest tolerated dose, there will be an additional nine-week follow-up period for those patients who respond to and tolerate either niacin treatment. Placebo-treated patients, or patients who have failed to respond to the niacin treatment will not participate in the follow-up portion but will receive appropriate treatment from their physician.

Hyperlipidemic patients not already on an appropriate diet will be stabilized on the American Heart Association Step 1 Diet (or equivalent) during the eight-week baseline period during which time lipid profiles will be determined at weeks 0, 4, 6 and 8. Patients will receive placebo tablets from week 4 (Visit 2). Baseline for patients already stabilized on a diet can be reduced to four weeks. All patients will receive placebo treatment for four weeks prior to entry into the Treatment Phase of the study.

The niacin given to the b.i.d. group was in the form of controlled release 250 mg, 500 mg and 750 mg tablets of Examples VI, V and I, respectively, hereinabove. The niacin given to the single dose groups was in also in the form of the 250 mg, 500 mg and 750 mg controlled release tablets.

At the end of the baseline period, patients who qualify for randomization into the treatment period will be assigned to either single dose niacin, b.i.d. niacin, or placebo treatment. Niacin dosage will be titrated to the highest tolerated dose (maximum 1.5 gm per day), and will remain on that dose for the four-week treatment period. Patient groups will receive niacin 250 mg b.i.d. dosed at breakfast and at the evening meal for one week, or 500 mg to be taken in a single dose with the evening meal. Then the dose will be increased to 500 mg b.i.d. or 1.0 g in one dose at the daily meal. Patients who cannot tolerate 500 mg b.i.d. for at least four weeks will be dropped from the study. After four weeks, the dose for those patients who do tolerate 500 mg b.i.d. will be increased to 750 mg b.i.d. or 1.5 g taken as two 750 mg tablets at the evening meal, for the next four weeks.

If necessary, during the first nine weeks of treatment, the dose may be reduced to 500 mg b.i.d. or 1.0 g in the single dose group, and the patient will be treated at the lower dose for at least nine consecutive weeks. Whenever possible, all patients who respond to the niacin treatment and tolerate it well will remain on their highest tolerated dose for an additional nine-week follow-up period. During the treatment period, fasting lipid profiles will be performed at each visit (the 3rd, 6th and 9th week of each phase).

At the conclusion of the study, the patients in the b.i.d. group and in the single dose group are found to exhibit substantially equivalent lowering of their LDL-C from baseline (avg.=12.5%), while the HDL-C levels of both groups also increase by an equivalent amount (avg.=22.5%). Significantly, 20% (n=20) of the b.i.d. niacin group exhibit at least one abnormal liver function test result (>1.5 times normal level), while only 2.5 (n=2) of the single dose niacin group exhibit an abnormal liver test result.

Thus, this trial demonstrates that a combination of single dose, prolonged release niacin in equivalent in its hypolipidemic effects to the same dose of controlled-release niacin given b.i.d., while exhibiting substantially fewer liver abnormalities.

All publications, patents and patent applications are herein incorporated by reference to the same extent as if each individual publication, patent, or patent application was specifically and individually indicated to be incorporated by reference.

It will be apparent to one of ordinary skill in the art that many changes and modifications can be made in the invention without departing from the spirit or scope of the appended claims.

What is claimed is:

1. A therapeutic method for lowering serum lipids or lipid components consisting essentially of administering to a human in need of such treatment an amount of a single daily dose of niacin which is effective to lower the nocturnal levels of a serum lipid or lipid component selected from the group consisting of total serum cholesterol, total triglycerides, lipoprotein a and low-density lipoprotein-cholesterol (LDL-C), wherein said dose of niacin is administered by ingestion of at least one controlled release tablet comprising, in admixture, about 5–30 % high viscosity hydroxypropyl methyl cellulose having a nominal viscosity, 2% aqueous solution, of at least about 10,000 cps, a methoxyl content of about 7–30% and a hydroxypropyl content of about 7–20%, about 2–15% of a water-soluble pharmaceutical binder, about 2–20% of a hydrophobic component and about 30–90% niacin.

2. The method of claim 1 wherein said treatment also raises the levels of high density lipoprotein cholesterol (HDL-C).

3. The method of claim 1 wherein the single dose of niacin is administered with the evening meal of said human or after the evening meal of said human but before bedtime.

4. The method of claim 1 wherein the tablet further comprises a coating comprising a water-swellable polymer.

5. The method of claim 4 wherein the coating of the water-swellable polymer is overcoated with an enteric coating.

6. The method of claim 1 wherein the tablet comprises about 50–85% niacin.

7. The method of claim 1 wherein the hydrophobic component comprises a wax.

8. The method of claim 1 wherein the hydroxypropyl methyl cellulose has a nominal viscosity, 2 percent aqueous solution, of about 50,000–100,000 cps.

9. The method of claim 8 wherein the hydroxypropylmethyl cellulose has a nominal viscosity, two percent solution, of about 100,000 cps, a methoxyl content of about 19–24%, a hydroxypropyl content of about 7–12 percent, and a particle size where at least ninety percent passes through a USS 100 mesh screen.

10. The method of claim 1 wherein the water-soluble pharmaceutical binder is selected form the group consisting low-viscosity hydroxypropyl methylcellulose which has a nominal viscosity, two percent solution, of less than about 100 cps, polyvinyl pyrollidone, methyl cellulose, gelatin, starch, sucrose and lactose.

11. The method of claim 1 wherein the tablet is a 250 mg tablet, a 500 mg tablet, a 750 mg tablet or mixtures thereof.

* * * * *

UNITED STATES PATENT AND TRADEMARK OFFICE
CERTIFICATE OF CORRECTION

PATENT NO. : 5,268,181

DATED : December 7, 1993

INVENTOR(S) : O'Neill et al.

It is certified that error appears in the above-identified patent and that said Letters Patent is hereby corrected as shown below:

At Column 4, lines 14, 18 and 28, please delete "CPS" and insert therefor --cps--; and line 27, please delete "HMPC" and insert therefor --HPMC--;

At Column 6, line 14, please delete "K1100MCR" and insert therefor --K100MCR--.

At Column 8, lines 34 and 35, please delete "Tablets having the composition shown in Example V were made using conventional and fluid bed techniques"; and at lines 55 and 65, please delete "$\geq$" and insert therefor --$\geq$--.

Signed and Sealed this

Tenth Day of October, 1995

Attest:

BRUCE LEHMAN

*Attesting Officer*   *Commissioner of Patents and Trademarks*